US00PP19418P2

(12) United States Plant Patent
van Diemen

(10) Patent No.: US PP19,418 P2
(45) Date of Patent: Nov. 4, 2008

(54) ***FICUS* PLANT NAMED 'AMSTEL GREEN GOLD'**

(50) Latin Name: *Ficus binnendijkii*
Varietal Denomination: Amstel Green Gold

(75) Inventor: Hubertus T. van Diemen, Nieuwveen (NL)

(73) Assignee: Kwekerij De Amstel B.V., Nieuwveen (NL)

( * ) Notice: Subject to any disclaimer, the term of this patent is extended or adjusted under 35 U.S.C. 154(b) by 0 days.

(21) Appl. No.: 11/710,833

(22) Filed: Feb. 26, 2007

(51) Int. Cl.
*A01H 5/00* (2006.01)

(52) U.S. Cl. ..... Plt./211

(58) Field of Classification Search ..... Plt./211
See application file for complete search history.

*Primary Examiner*—Kent L. Bell
*Assistant Examiner*—June Hwu

(57) ABSTRACT

A new cultivar of *Ficus* plant named 'Amstel Green Gold' that is characterized by reddish green young leaves and green mature leaves.

1 Drawing Sheet

Botanical classification: *Ficus binnendijkii.*
Variety denomination: 'Amstel Green Gold'.

BACKGROUND OF THE INVENTION

The present invention relates to a new and distinct cultivar of *Ficus* plant botanically known as *Ficus binnendijkii* and hereinafter referred to by the cultivar name 'Amstel Green Gold'.

The new cultivar was discovered by the inventor in a greenhouse in a cultivated area of De Kwakel, The Netherlands in the spring of 2004. 'Amstel Green Gold' was discovered as a naturally occurring branch mutation of *Ficus binnendijkii* 'Amstel Gold' (not patented).

Asexual reproduction by terminal cuttings of the new cultivar 'Amstel Green Gold' was first done in 2005 in De Kwakel, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Ficus* cultivar 'Amstel Green Gold'.

1. *Ficus* 'Amstel Green Gold' exhibits green mature leaves.
2. *Ficus* 'Amstel Green Gold' exhibits reddish green young leaves.

The closest comparison cultivar is the parent plant *Ficus* 'Amstel Gold'. The new cultivar 'Amstel Green Gold' is distinguishable from 'Amstel Gold' by the following characteristics:

1. 'Amstel Green Gold' has a more reddish color in young leaves than the leaves of 'Amstel Gold'.
2. 'Amstel Green Gold' has a greener color in mature leaves than the leaves of 'Amstel Gold'.

BRIEF DESCRIPTION OF THE DRAWING

The accompanying photograph illustrates the distinguishing traits of *Ficus* 'Amstel Green Gold'. The plant in the photograph shows an overall view of a 10 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Ficus* cultivar named 'Amstel Green Gold'. Data was collected in De Kwakel, The Netherlands from 10 month old greenhouse grown plants in 15 cm. containers. The time of year was Fall and the average temperature was 23 degrees Centigrade during the day and 20 degrees Centigrade at night. No photoperiodic treatments were used. Color determinations are in accordance with The Royal Horticultural Society Colour Chart 2001 edition, except where general color terms of ordinary dictionary significance are used. The growing requirements are similar to the species. 'Amstel Green Gold' has not been tested under all possible conditions and phenotypic differences may be observed with variations in environmental, climatic, and cultural conditions, however, without any variance in genotype.

Botanical classification: *Ficus binnendijkii* 'Amstel Green Gold'.
Use: Ornamental.
Parentage: 'Amstel Green Gold' is a naturally occurring branch mutation of *Ficus* 'Amstel Gold'.
Vigor: Low to moderate.
Growth rate: 5 cm. per month.
Growth habit: Upright.
Plant shape: Conical.
Suitable container size: 15 cm. diameter container.
Height: Average 72 cm.
Width: Average 59 cm.
Hardiness: USDA Zone 10.
Propagation: Terminal cuttings.
Time to initiate roots: Approximately 14 days to produce roots on an initial cutting at 22° Centigrade.
Time to produce a rooted cutting: Approximately 30 days to produce a rooted cutting at 22° Centigrade.

Crop time: 10 months.
Root system: Fine and fibrous.
Stem:
*Branching habit.*—Moderately branching.
*Basal branches.*—3 basal branches grow from the base.
*Average number of lateral branches.*—32.
*Pinching.*—No.
*Lateral branch diameter.*—2.0 mm. in diameter.
*Lateral branch length.*—11.8 cm. in length.
*Lateral branch strength.*—Moderately strong.
*Stem color.*—Young twigs 137A to 189A to 194A; mature bark N199B.
*Pubescence.*—Absent.
*Internode length.*—2.6 cm. between nodes.
*Shape.*—Rounded.
*Surface.*—Glossy and rounded.
*Stem strength.*—Strong.
*Other characteristics.*—A rubbery substance will be emitted when branches are damaged.
Foliage:
*Leaf arrangement.*—Alternate.
*Compound or single.*—Single.
*Leaf shape.*—Narrow oblong to linear.
*Leaf apex.*—Long apiculate.
*Leaf base.*—Rounded.
*Leaf texture* (*upper surface*).—Moderately glossy.
*Leaf length.*—Average 17.5 cm. in length.
*Leaf width.*—1.9 cm. in width.
*Quantity of leaves per lateral branch.*—Average 5.
*Pubescence.*—Absent.
*Leaf margin.*—Entire, only very slightly repand.
*Vein pattern.*—Pinnate.
*Young leaf color,* (*upper surface*).—151A to 151B; centers irregularly blotched 146A to 146B.
*Young leaf color,* (*lower surface*).—151B; centers irregularly blotched 147C.
*Mature leaf color,* (*upper surface*).—143A to 143B; centers irregularly blotched 147A.
*Mature leaf color,* (*lower surface*).—144A; centers irregularly blotched 146B to 146C.
*Vein color* (*lower surface*).—144B to 144C.
*Vein color* (*upper surface*).—143C.
*Leaf attachment.*—Petiolate.
*Petiole dimensions.*—Average 1.2 cm. in length and 2 mm. in diameter.
*Petiole color.*—Upper side 143B; under side 144A to 144B.
*Petiole texture.*—Smooth.
*Durability of foliage to stress.*—High.
*Other characteristics.*—Leaves are leathery.
*Stipules.*—Absent.
Flowers: Flowers have not been observed.
Disease and insect resistance: Plants of the new *Ficus* have not been observed for disease or insect resistance.

It is claimed:

1. A new and distinct variety of *Ficus* plant named 'Amstel Green Gold' as described and illustrated.

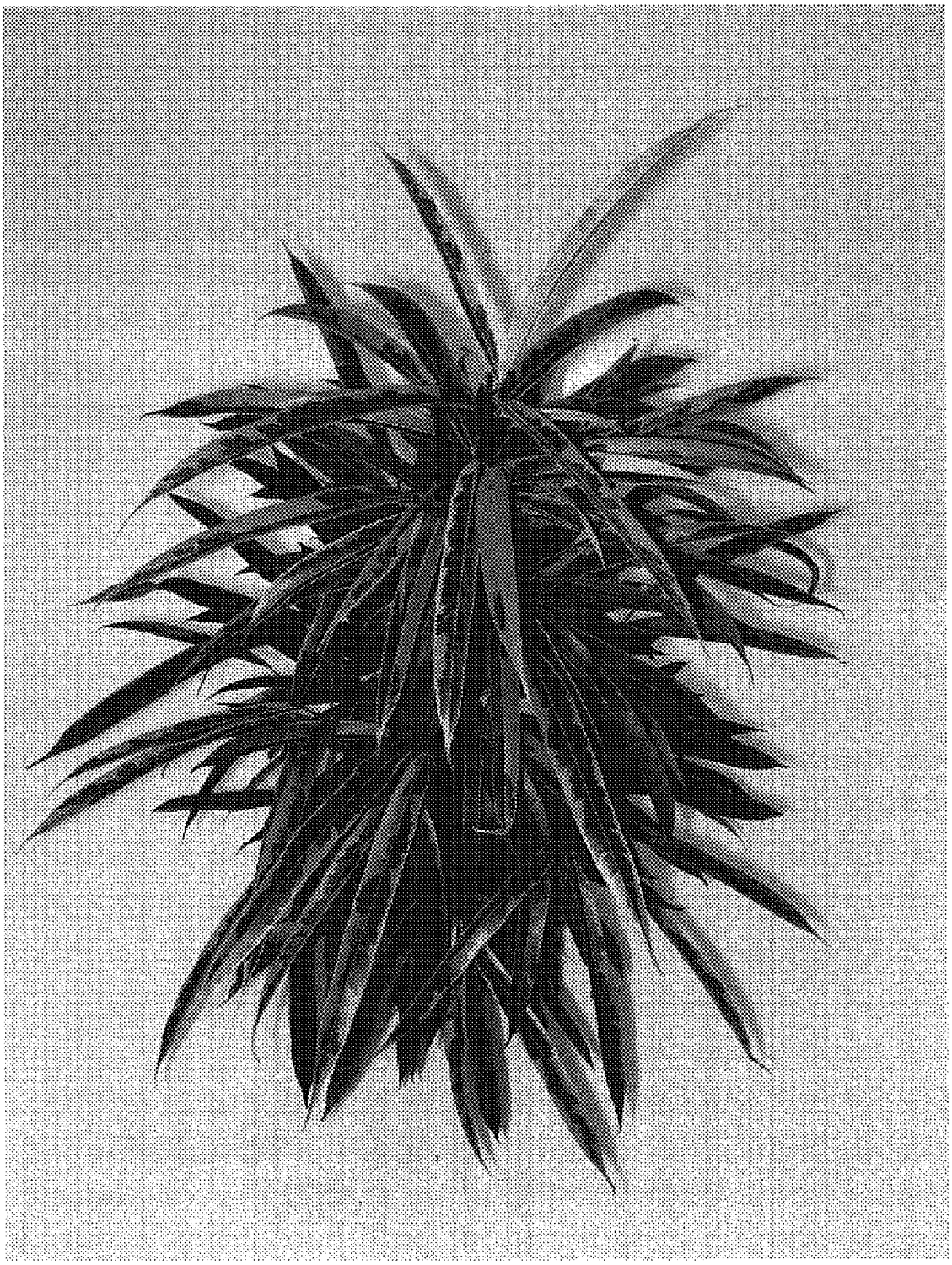

* * * * *